US009067179B2

(12) United States Patent
Charest et al.

(10) Patent No.: US 9,067,179 B2
(45) Date of Patent: Jun. 30, 2015

(54) MICROFLUIDIC DEVICE FACILITATING GAS EXCHANGE, AND METHODS OF USE AND MANUFACTURE THEREOF

(75) Inventors: Joseph L. Charest, Cambridge, MA (US); Jeffrey T. Borenstein, Newton, MA (US); Joseph M. Bauer, Whitman, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 12/981,903

(22) Filed: Dec. 30, 2010

(65) Prior Publication Data

US 2011/0158847 A1 Jun. 30, 2011

Related U.S. Application Data

(60) Provisional application No. 61/291,560, filed on Dec. 31, 2009.

(51) Int. Cl.
*A61M 1/16* (2006.01)
*B01D 69/06* (2006.01)
*A61M 1/14* (2006.01)
*B01D 63/08* (2006.01)
*B01D 67/00* (2006.01)
*B01D 69/02* (2006.01)

(52) U.S. Cl.
CPC .......... *B01D 69/06* (2013.01); *Y10T 29/49826* (2015.01); *A61M 1/16* (2013.01); *A61M 1/14* (2013.01); *A61M 1/1698* (2013.01); *A61M 2206/11* (2013.01); *B01D 63/081* (2013.01); *B01D 63/082* (2013.01); *B01D 63/085* (2013.01); *B01D 67/0009* (2013.01); *B01D 69/02* (2013.01); *B01D 2325/04* (2013.01)

(58) Field of Classification Search
CPC ....... A61M 1/14; A61M 1/16; A61M 1/1625; A61M 1/1678; A61M 1/1698; A61M 1/32; A61M 2206/11; B01D 63/08; B01D 63/081; B01D 63/082; B01D 63/085; B01D 67/0009; B01D 69/02; B01D 69/06; B01D 2325/04; Y10T 29/49826
USPC ................. 422/44–46; 117/68; 210/321.71
See application file for complete search history.

(56) References Cited

U.S. PATENT DOCUMENTS

| 2,876,769 A | 3/1959 | Cordova |
| 3,489,647 A | 1/1970 | Kolobow |
| 3,738,813 A | 6/1973 | Esmond |

(Continued)

FOREIGN PATENT DOCUMENTS

| DE | 10 2008 045 621 A1 | 3/2010 |
| EP | 0 416 92 | 12/1981 |

(Continued)

OTHER PUBLICATIONS

Alex C. M. Kuo, Poly(dimethylsiloxane), Polymer data handbook, 1999 Oxford University Press, Inc.*

(Continued)

*Primary Examiner* — Philip R Wiest
*Assistant Examiner* — Benjamin Klein
(74) *Attorney, Agent, or Firm* — Edward A. Gordon; Foley & Lardner LLP

(57) ABSTRACT

The invention provides systems and methods for exchanging gas in a microfluidic device, and methods for preparing such microfluidic devices. The systems and methods can be used to transfer oxygen to blood to assist lung function in a patient.

21 Claims, 4 Drawing Sheets

(56) References Cited

U.S. PATENT DOCUMENTS

| | | | |
|---|---|---|---|
| 3,847,211 A * | 11/1974 | Fischel et al. | 165/166 |
| 4,620,965 A | 11/1986 | Fukusawa et al. | |
| 4,756,835 A * | 7/1988 | Wilson | 210/651 |
| 4,997,565 A | 3/1991 | Niesen | |
| 5,207,639 A | 5/1993 | Cooper | |
| 5,254,259 A | 10/1993 | Bellhouse et al. | |
| 6,241,945 B1 | 6/2001 | Owen | |
| 6,514,412 B1 | 2/2003 | Insley et al. | |
| 6,602,468 B2 | 8/2003 | Patterson et al. | |
| 7,713,544 B2 | 5/2010 | Chaikof et al. | |
| 7,759,113 B2 | 7/2010 | Vacanti et al. | |
| 7,955,504 B1 | 6/2011 | Jovanovic et al. | |
| 8,128,822 B2 * | 3/2012 | Browning et al. | 210/321.71 |
| 8,137,554 B2 * | 3/2012 | Jovanovic et al. | 210/321.71 |
| 8,266,791 B2 | 9/2012 | Borenstein et al. | |
| 2002/0182241 A1 | 12/2002 | Borenstein et al. | |
| 2003/0121841 A1 | 7/2003 | Harttig et al. | |
| 2003/0175149 A1 | 9/2003 | Searles et al. | |
| 2005/0202557 A1 | 9/2005 | Borenstein et al. | |
| 2006/0136182 A1 | 6/2006 | Vacanti et al. | |
| 2006/0173394 A1 * | 8/2006 | Stroock et al. | 602/41 |
| 2007/0119771 A1 * | 5/2007 | Schukar et al. | 210/321.77 |
| 2008/0093298 A1 | 4/2008 | Browning et al. | |
| 2009/0081079 A1 * | 3/2009 | Johns | 422/46 |
| 2009/0234332 A1 | 9/2009 | Borenstein et al. | |
| 2010/0098742 A1 | 4/2010 | Vacanti et al. | |
| 2010/0118642 A1 | 5/2010 | Ho et al. | |
| 2010/0267136 A1 | 10/2010 | Vacanti et al. | |
| 2011/0158847 A1 | 6/2011 | Charest et al. | |
| 2011/0186165 A1 | 8/2011 | Borenstein et al. | |
| 2011/0226686 A1 | 9/2011 | Maurer | |
| 2012/0182609 A1 | 7/2012 | Borenstein et al. | |

FOREIGN PATENT DOCUMENTS

| | | |
|---|---|---|
| GB | 1 408 562 | 10/1975 |
| JP | 62-064372 | 3/1987 |
| JP | 2003-093853 | 4/2003 |
| WO | WO-02/076529 | 10/2002 |
| WO | WO-2006/042079 A1 | 4/2006 |
| WO | WO-2010/025926 | 3/2010 |
| WO | WO-2011/150216 | 12/2011 |

OTHER PUBLICATIONS

Burgess, K. et al., "Towards microfabricated biohybrid artificial lung modules for chronic respiratory support," Biomedical Microdevices, vol. 11, No. 12 Aug. 2008, pp. 117-127.

International Preliminary Report on Patentability dated Dec. 6, 2012, International application No. PCT/US2011/038148, International filing date May 26, 2011.

International Preliminary Report on Patentability mailed Jul. 12, 2012, International application No. PCT/US2010/062537, International filing date Dec. 30, 2010.

International Search Report and Written Opinion, International application No. PCT/US2012/067971, International filing date Dec. 5, 2012.

International Search Report, International Application No. PCT/US2010/062537, International Filing Date Dec. 30, 2010.

US Notice of Allowance on 102590-0246 DTD Jun. 14, 2013.

Borenstein et al., "Microfabrication Technology for Vascularized Tissue Engineering," Biomedical Microdevices, 4(3):167-175 (2002).

Hongkai et al., "Construction of Microfluidic Chips Using Polydimethylsiloxane for Adhesive Bonding," Lab on a Chip, 5:1393-1398 (2005).

International Preliminary Report on Patentability mailed on Jun. 19, 2014 in PCT Application No. PCT/US2012/067971.

International Search Report in PCT/US2011/038148, dated Aug. 26, 2011.

LeClerc et al., "Cell Culture in 3-Dimensional Microfluidic Structure of PDMS (polydimethylsiloxane)," Biomedical Microdevices, 5(2):109-114 (2003).

Notice of Allowance in U.S. Appl. No. 13/116,219 dated Oct. 4, 2013.

Stroock, et al., "Chaotic Mixer for Microchannels", Science, vol. 295, Jan. 25, 2002, pp. 647-651.

US Office Action in U.S. Appl. No. 13/705,795 dated May 16, 2014.

Wu et al., "Construction of Microfluidic Chips Using Polydimethylsiloxane for Adhesive Bonding," Lab on a Chip, 5:1393-1398 (2005).

Yasuda, H. "Units of Gas Permeability Constants", Journal of Applied Polymer Science, 1975, vol. 19, pp. 2529-2536.

First Office Action issued in Australian Patent Application No. 2010339409 dated Sep. 29, 2014.

First Office Action issued on Jul. 17, 2014 in Chinese Patent Application No. 2011800367123.

Office Action issued Dec. 4, 2014 in Japanese Patent Application No. 2012-547304.

Patent Examination Report No. 1 in Australian Patent Application No. 2011258203, dated Nov. 4, 2014.

US Office Action on U.S. Appl. No. 13/705,795 DTD Oct. 22, 2014.

Office Action issued Mar. 26, 2015 in Japanese Patent Application No. 2013-512244.

US Office Action in U.S. Appl. No. 13/705,795 DTD Mar. 13, 2015.

\* cited by examiner

MICROFLUIDIC DEVICE FACILITATING GAS EXCHANGE, AND METHODS OF USE AND MANUFACTURE THEREOF

RELATED APPLICATIONS

This application claims the benefit of and priority to U.S. Provisional Patent Application Ser. No. 61/291,560, filed Dec. 31, 2009, the contents of which are hereby incorporated by reference for all purposes.

FIELD OF THE INVENTION

The invention provides systems and methods for exchanging gas in a microfluidic device, and methods for preparing such microfluidic devices.

BACKGROUND OF THE INVENTION

Various systems and methods for facilitating gas exchange with a fluid have been described in the literature. One application of such systems and methods are for use in lung assist technologies, which supplement the function of a damaged lung in a patient. Another application of such systems and methods are for use in industrial processes where it is desirable to exchange gas in fluid.

Certain systems and methods described previously facilitate gas exchange with a fluid using hollow fiber membranes and/or thin sheet membranes. Generally, hollow fiber membranes are thin-walled, gas-permeable hollow fibers, which permit gas exchange between gas in the core of the fiber and fluid (e.g., blood) surrounding the fiber. A hollow fiber device typically includes a bundle of hollow fibers that is connected to a gas inlet and outlet. The fibers may be enclosed in a housing, which may be connected to a blood inlet and outlet. Blood flow is typically transverse the axis of the fibers.

Systems and methods that utilize a thin-sheet membrane to facilitate gas exchange generally have a thin sheet of gas permeable material separating a fluid chamber (e.g., a chamber for blood) from a gas chamber. Gas exchange occurs across the membrane between the two chambers, and the membrane and chambers can be rolled or folded to create a convenient form factor. The entire membrane and chambers can be enclosed within a housing that provides blood and gas inlets and outlets.

Systems for gas exchange utilizing a hollow fiber membrane and/or thin sheet membrane feature several disadvantages. First, hollow fiber membranes often have geometrically limited surface-to-volume ratios and limited control of blood flow patterns. For example, a round cross section geometry and fiber packing density of hollow fiber membranes limits the surface-to-volume ratio, thereby creating a performance limit. Second, the fiber packing geometry often does not allow for a tight control of the blood flow path, nor does it allow for precision engineering to mimic human vascular physiology. Since the blood flow path influences shear stress and other blood flow characteristics that impact blood health, hollow fiber membranes generally do not provide a means to control or limit damage to patient blood. For their part, thin sheet membranes often have limited gas transfer due to, for example, blood side boundary layer conditions, restrictions on blood chamber height, and blood and gas chamber configurations that limit gas exchange to two directions. In addition, thin sheet membranes are often fairly thick, having for example, a thickness of at least 75 μm, since the membranes may be unsupported in certain areas.

Accordingly, a need exists for improved systems and methods of exchanging gas in a microfluidic device. The present invention addresses this need and provides other related advantages.

SUMMARY

The invention provides microfluidic devices, methods for facilitating gas exchange with a fluid, and methods for manufacturing a microfluidic device. The microfluidic devices may be used in medical applications or industrial applications where it is desirable to transfer a gas to or from a fluid. For example, microfluidic devices and methods described herein are contemplated to provide particular advantages in transferring oxygen to blood and to be applicable for use as an artificial lung device. Microfluidic devices described herein contain at least one layer of a single type of gas permeable material, and the layer contains at least one chamber for gas flow and at least one chamber for fluid flow. The thickness of gas permeable material separating any chamber for gas flow from an adjacent chamber for fluid flow is minimized so that gas can pass through the gas permeable material and into fluid in the chamber for fluid flow. Features of the chamber for fluid flow, such as height, width, length, and shape can be optimized to maximize transfer of gas to and/or from a fluid, and also provide superior fluid flow properties for transmission of fluid, such as blood, through the device.

Accordingly, one aspect of the invention provides a microfluidic device, comprising a first layer of a single type of gas permeable material that defines therein at least one chamber for gas flow and at least one chamber for fluid flow, wherein the thickness of gas permeable material separating any chamber for gas flow from an adjacent chamber for fluid flow is about 1 μm to about 100 μm.

Another aspect of the invention provides a microfluidic device, comprising a first layer of a single type of gas permeable material that defines therein at least one chamber for gas flow and at least one chamber for fluid flow, wherein the thickness of gas permeable material separating any chamber for gas flow from an adjacent chamber for fluid flow is no greater than that which has an oxygen gas permeance of at least $1 \times 10^{-6}$ mL/s/cm$^2$/cm Hg.

Another aspect of the invention provides a method for transferring a gas to a fluid. The method comprises passing a fluid through a microfluidic device described herein having a gas in at least one chamber for gas flow, to thereby transfer said gas to said fluid.

A further aspect of the invention provides a method of manufacturing a microfluidic device. The method comprises forming a first layer of a single type of gas permeable material that defines therein at least one chamber for gas flow and at least one chamber for fluid flow, wherein the thickness of gas permeable material separating any chamber for gas flow from an adjacent chamber for fluid flow is about 1 μm to about 100 μm.

These and other aspects, along with other features and embodiments of the invention herein disclosed herein, will become more apparent through reference to the following description, drawings, and claims. Furthermore, it is to be understood that the aspects, features, and embodiments described herein are not mutually exclusive and can exist in various combinations and permutations.

BRIEF DESCRIPTION OF FIGURES

Figure 1:
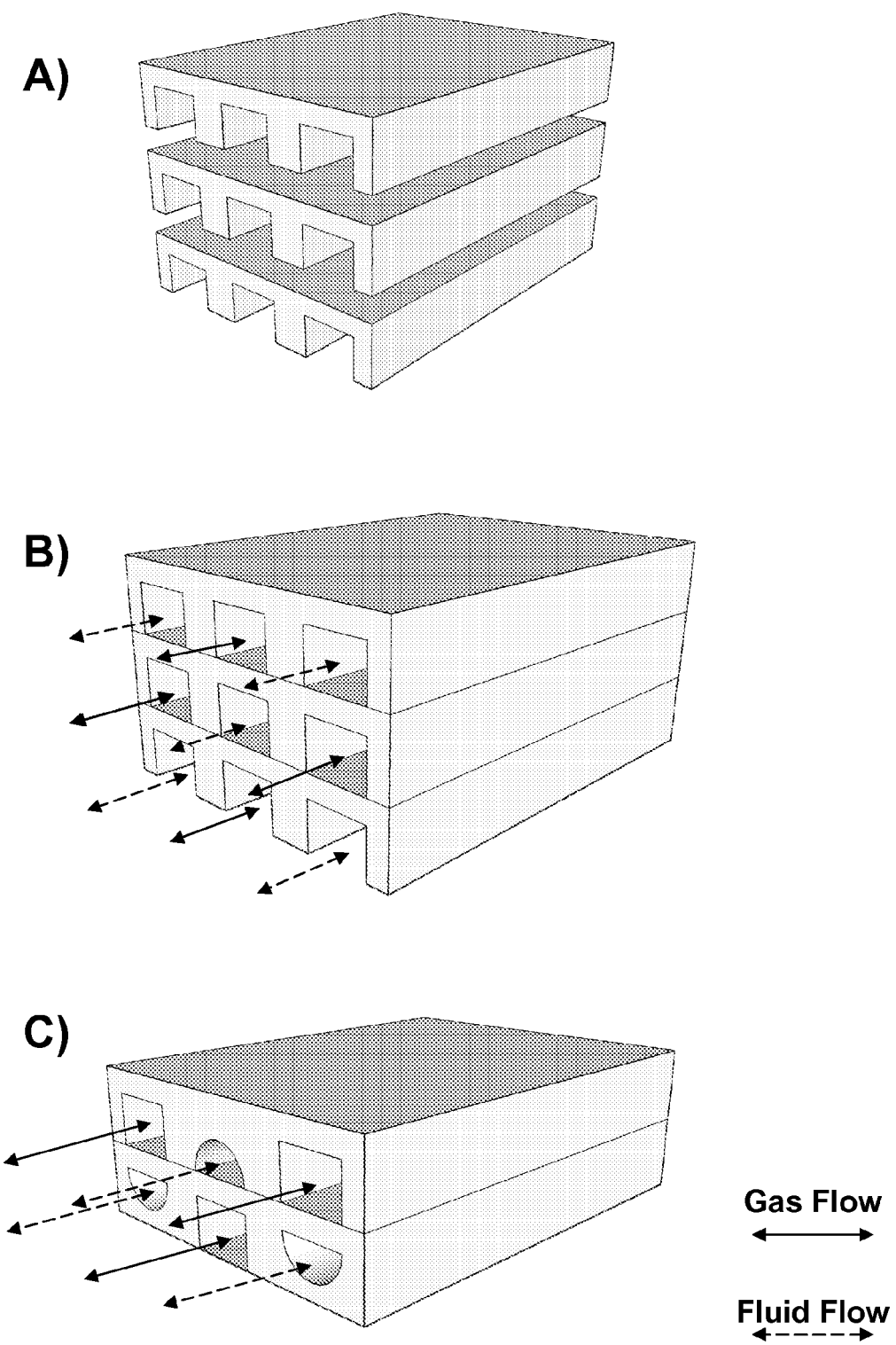

FIG. 1 depicts a cross-sectional schematic of two microfluidic device configuration of the invention having parallel/ anti-parallel fluid and gas flow configurations. Unassembled layers are shown in FIG. 1A and assembled layers are shown in FIGS. 1B and 1C. Shown are two or three layers with three chambers each; however, there may be any number of chambers or layers. Integrating fluid chambers and gas chambers within the layers allows for an increased variety of configurations, which can increase the potential interfaces for gas exchange. In this configuration, gas and fluid flow paths are either parallel or anti-parallel.

Figure 2:
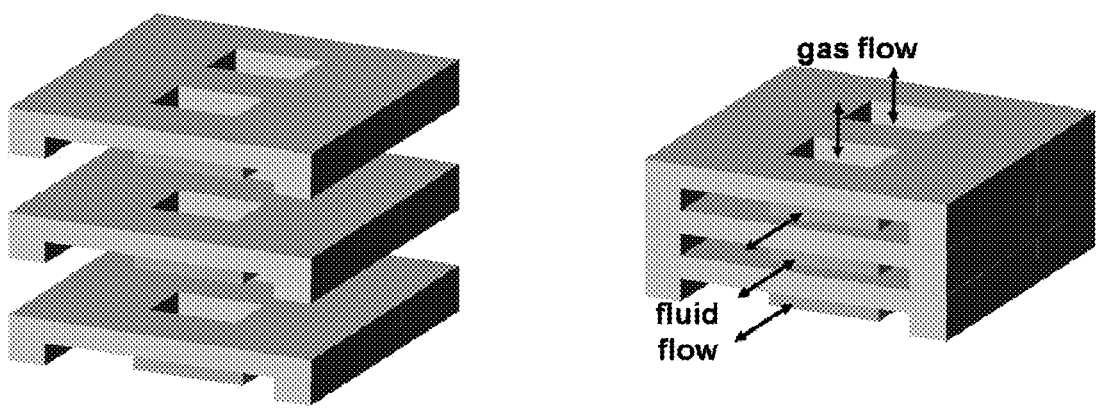

FIG. 2 depicts a cross-sectional schematic of one microfluidic device configuration of the invention having fluid flow and gas flow transverse to each other. Unassembled layers are shown on the left and assembled layers are shown on the right. Shown are three layers each having one fluid chamber and two gas chambers; however, there may be any number of layers and/or chambers. Integrating fluid and gas chambers within the layers allows for an increased variety of configurations, which can increase the potential interfaces and therefore surface area for gas exchange. In this configuration, gas flow and fluid flow are transverse to each other and each layer is configured similarly; however, the configuration can change for each layer.

Figure 3:
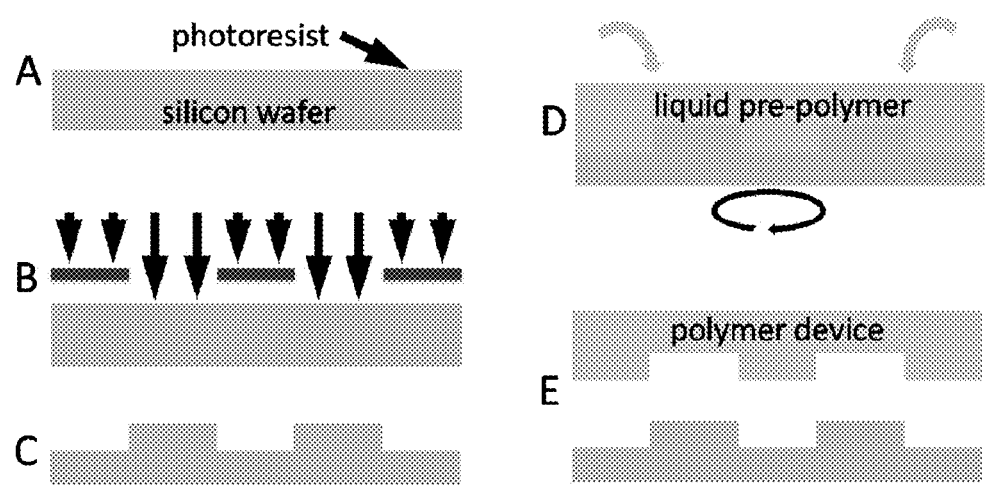

FIG. 3 depicts an exemplary, general method for preparing a microfluidic device having multiple chambers, whereby chamber layers are fabricated by: A) coating a silicon wafer with photoresist, B) photolithographically patterning, C) developing the photoresist to create a mold, D) then a liquid pre-polymer may then be spin-coated into the mold and (E) released to create the polymer device. An alternative method of fabrication involves curing the prepolymer with an upper mold that applies pressure to the prepolymer.

Figure 4:
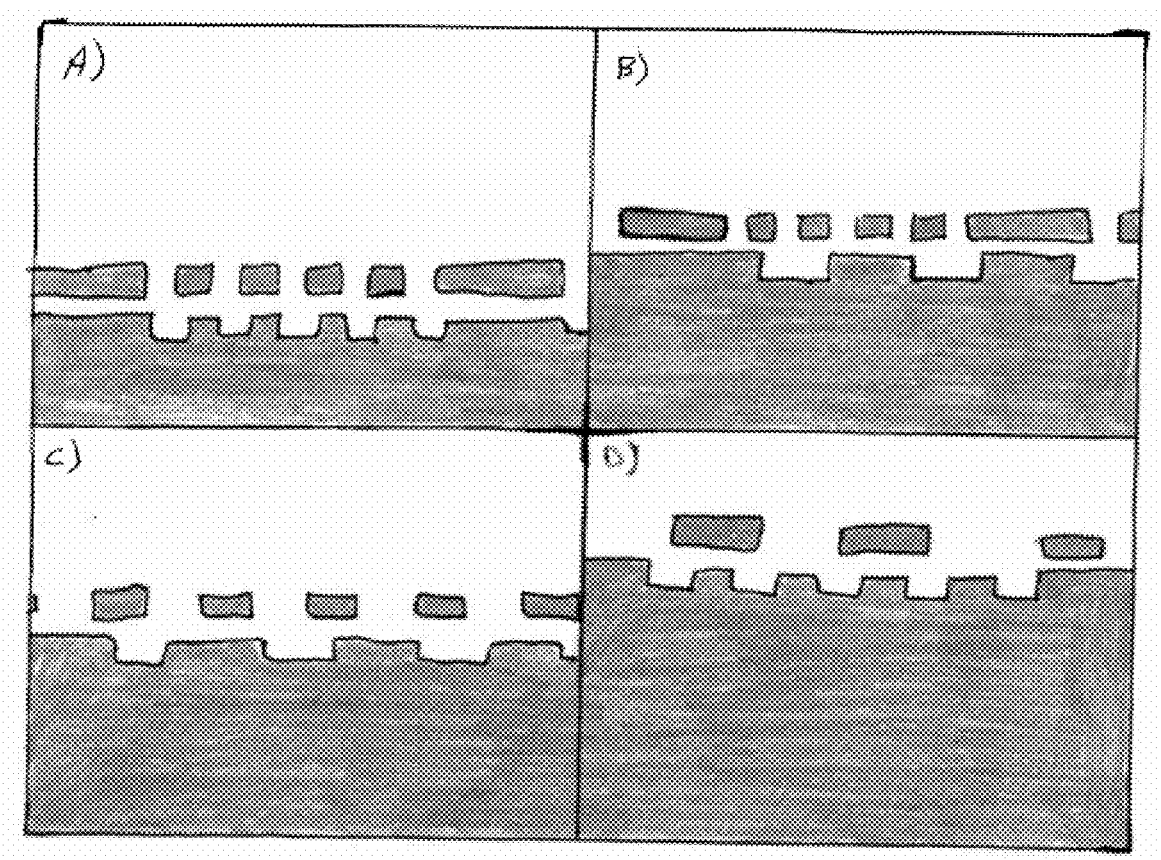

FIG. 4 depicts cross-section views of microfluidic devices fabricated in polydimethylsiloxane (PDMS). Two layers are shown in FIG. 4, though a variety of channel and layer attachment configurations can be achieved as explained in the detailed description. As illustrated, chamber dimensions can be substantially equal for each layer (See Part A) or vary from layer to layer (See Parts B through D).

DETAILED DESCRIPTION

The invention provides microfluidic devices, methods for facilitating gas exchange with a fluid, and methods for manufacturing a microfluidic device. As explained above, the microfluidic devices may be used in medical applications or industrial applications where it is desirable to transfer a gas to and/or from a fluid. The microfluidic devices and methods are contemplated to provide particular advantages in transferring oxygen to blood and to be applicable for use in an artificial lung device. For example, fluid chamber features described herein are contemplated to reduce the occurrence of blood clotting, hemolysis, inflammation, and other side effects that a patient may experience due to use of a lung assist gas exchange device. Also, the configuration of the fluid chambers provides superior surface-to-volume ratios, which are contemplated to improve gas transfer efficiency. Still further, positioning both a gas chamber and a fluid chamber in the same layer of a single type of gas permeable material provides a microfluidic device that is more amenable to manufacturing techniques and production on large scale. Various aspects of the invention are set forth below in sections; however, aspects of the invention described in one particular section are not to be limited to any particular section.

I. Microfluidic Devices for Transfer of a Gas

Microfluidic devices described herein contain at least one layer of a single type of gas permeable material, and the layer contains at least one chamber for gas flow and at least one chamber for fluid flow. The thickness of gas permeable material separating any chamber for gas flow from an adjacent chamber for fluid flow is minimized so that gas can pass through the gas permeable material and into fluid in the chamber for fluid flow. Features of the chamber for fluid flow can be selected as described below in order to achieve certain performance characteristics.

Accordingly, one aspect of the invention provides a microfluidic device comprising a first layer of a single type of gas permeable material that defines therein at least one chamber for gas flow and at least one chamber for fluid flow, wherein the thickness of gas permeable material separating any chamber for gas flow from an adjacent chamber for fluid flow is about 1 μm to about 100 μm. Positioning of a chamber for gas flow adjacent to and in such close proximity to a chamber for fluid flow permits gas to penetrate through the gas permeable material separating the chamber for gas flow from the chamber for fluid flow, to thereby transfer gas to and/or from the fluid. For example, when the chamber for fluid flow contains blood, and the chamber for gas flow contains oxygen, oxygen can be transferred to the blood and carbon dioxide and/or other gases dissolved in the blood can transfer to the chamber for gas flow. This transmission of gas mimics the exchange of gas performed by lungs in a patient. In certain embodiments, the thickness of gas permeable material separating any chamber for gas flow from an adjacent chamber for fluid flow is about 10 μm to about 100 μm.

Another aspect of the invention provides a microfluidic device comprising a first layer of a single type of gas permeable material that defines therein at least one chamber for gas flow and at least one chamber for fluid flow, wherein the thickness of gas permeable material separating any chamber for gas flow from an adjacent chamber for fluid flow is no greater than that which has an oxygen gas permeance of at least $1 \times 10^{-6}$ mL/s/cm$^2$/cm Hg. It is contemplated that various types of gas permeable materials can be used to prepare the microfluidic device, and the configuration of the microfluidic device is such that gas is able to penetrate through the gas permeable material at a rate sufficient to transfer sufficient gas to and/or from the fluid for a particular application.

Because different gas permeable materials have different permeance properties for transfer of a gas, the thickness of the gas permeable material separating the chamber for gas flow from the chamber for fluid flow can be characterized according to the thickness that permits gas transfer at a particular rate. Accordingly, in certain embodiments, the thickness of gas permeable material separating any chamber for gas flow from an adjacent chamber for fluid flow is no greater than that which has an oxygen gas permeance of at least $1 \times 10^{-6}$ mL/s/cm$^2$/cm Hg, $1 \times 10^{-5}$ mL/s/cm$^2$/cm Hg, $3 \times 10^{-5}$ mL/s/cm$^2$/cm Hg, $7 \times 10^{-5}$ mL/s/cm$^2$/cm Hg, or $1 \times 10^{-4}$ mL/s/cm$^2$/cm Hg. In certain embodiments, the thickness of gas permeable material separating any chamber for gas flow from an adjacent chamber for fluid flow is such that the thickness provides oxygen gas permeance of in the range of about $1 \times 10^{-6}$ mL/s/cm$^2$/cm Hg to about $1 \times 10^{-3}$ mL/s/cm$^2$/cm Hg, or about $1 \times 10^{-5}$ mL/s/cm$^2$/cm Hg to about $7 \times 10^{-5}$ mL/s/cm$^2$/cm Hg.

In certain other embodiments, the thickness of gas permeable material separating any chamber for gas flow from an adjacent chamber for fluid flow is no greater than that which has carbon dioxide gas permeance of at least $1 \times 10^{-6}$ mL/s/cm$^2$/cm Hg, $1 \times 10^{-5}$ mL/s/cm$^2$/cm Hg, $2 \times 10^{-5}$ mL/s/cm$^2$/cm Hg, or $5 \times 10^{-5}$ mL/s/cm$^2$/cm Hg.

II. Arrangement of Chambers for Gas Flow and Chambers for Fluid Flow

The number and arrangement of chambers for gas flow and/or chambers for fluid flow can be adjusted to achieve particular performance properties for the microfluidic device. For example, increasing the number of chambers for gas flow in proximity to a chamber for fluid flow can increase the rate at which gas is transferred to the fluid. Similarly, reducing the thickness of gas permeable material separating a chamber for gas flow from a chamber for fluid flow can increase the rate at which gas is transferred to the fluid. Additional features of the microfluidic device that can be adjusted include (1) selecting the number of layers in the device containing chambers, and (2) selecting the orientation of chambers in one layer relative to the chambers in an adjacent layer.

Accordingly, in certain embodiments, the first layer defines therein a plurality of chambers for gas flow and a plurality of chambers for fluid flow, and the thickness of gas permeable material separating any chamber for gas flow from an adjacent chamber for fluid flow is about 1 μm to about 100 μm. In certain embodiments, the thickness of gas permeable material separating any chamber for gas flow from an adjacent chamber for fluid flow is about 10 μm to about 100 μm. In certain embodiments, the thickness of gas permeable material separating any chamber for gas flow from an adjacent chamber for fluid flow is about 10 μm to about 50 μm, or about 10 μm to about 25 μm. The number of chambers for gas flow in a layer may be greater than 20, 50, 100, 500, or 1000. The number of chambers for fluid flow in a layer may be greater than 20, 50, 100, 500, or 1000. In certain embodiments, the ratio of chambers for fluid flow compared to the number of chambers for gas flow may be in the range of 1:4 to 4:1, or 1:2 to 2:1.

The arrangement of chambers for gas flow and chambers for fluid flow in each layer can be selected to achieve particular performance properties. For example, in certain embodiments, each chamber for fluid flow is located between two chambers for gas flow. The arrangement of chambers can be selected so that within the same layer, there is an alternating occurrence of a chamber for gas fluid flow adjacent to a chamber for fluid flow. As noted above, increasing the number of chambers for gas flow that are in close proximity to a chamber for fluid flow is contemplated to increase the rate of gas transfer to and/or from the fluid.

The orientation of a chamber for gas flow relative to a chamber for fluid flow can be characterized according to the flow direction of gas and/or fluid traversing through the chamber. For example, in certain embodiments, any chamber for gas flow and any chamber for fluid flow are arranged such that flow directions for the gas and the fluid are parallel or anti-parallel to one another. FIG. 1 schematically depicts an orientation having parallel/anti-parallel fluid and gas flow directions. Alternatively, at least one chamber for gas flow is arranged such that the flow direction of gas is transverse to the direction of fluid flow in the chamber for fluid flow. FIG. 2 schematically depicts an orientation having transverse fluid and gas flow directions. It is contemplated that a configuration with multiple flow configurations within the same layer may improve gas exchange by increasing the opportunity to locate fluid channels in proximity to gas channels. An additional benefit to having multiple fluid types within one layer is that a device may consist of one single layer, while incorporating much of the functionality of a multi-layer device. Another way to characterize the orientation of chambers in the same layer is according to whether the chambers for gas flow are in-plane with the chambers for fluid flow, or perpendicular to the plane of the chambers for fluid flow.

The microfluidic device may contain multiple layers. For example, the microfluidic device may comprise a second layer of a single type of gas permeable material stacked upon the first layer, where the second layer defines therein at least one chamber for gas flow and at least one chamber for fluid flow. In certain embodiments, the microfluidic device may further comprise a third layer of a single type of gas permeable material stacked upon the second layer, where the third layer defines therein at least one chamber for gas flow and at least one chamber for fluid flow. Microfluidic devices containing multiple layers can allow for gas exchange between layers and within layers, and coordination of channel placement within layers with multilayer alignment may be employed to enhance overall gas exchange.

The thickness of the gas permeable materials separating chambers in the second layer can be selected to optimize the performance properties of the microfluidic device. For example, in certain embodiments, the thickness of gas permeable material separating a chamber for gas flow in the second layer from a chamber for fluid flow in the second layer is about 1 μm to about 100 μm, about 10 μm to about 100 μm, or about 10 μm to about 25 μm.

The orientation of chambers in one layer can be coordinated with the orientation of chambers in one or more adjacent layers. For example, in certain embodiments, any chambers for fluid flow in a layer are positioned between two chambers for gas flow in the same layer, and said chambers for fluid flow are aligned vertically with a chamber for gas flow in any adjacent layer. Such an orientation is contemplated to provide superior rates for gas transfer to a fluid because it increases the number of chambers for gas flow that are in close proximity to the chamber for fluid flow.

Further, as noted above, the thickness of gas permeable material separating a chamber for gas flow in the microfluidic device from a chamber for fluid flow can be selected to achieve a particular performance property. This thickness can be selected not only for chambers for gas flow and fluid flow in the same layer, but also between a chamber for gas flow in one layer and a chamber for fluid flow in an adjacent layer. Accordingly, in certain embodiments, the thickness of gas permeable material separating any chamber for gas flow in the microfluidic device from a chamber for fluid flow in the microfluidic device is about 1 μm to about 100 μm, or about 10 μm to about 100 μm. In certain other embodiments, the thickness of gas permeable material separating any chamber for gas flow in a layer from a chamber for fluid flow in the same layer is about 50 μm to about 100 μm. In certain other embodiments, the thickness of gas permeable material separating any chamber for gas flow in a layer from a chamber for fluid flow in the same layer is about 10 μm to about 25 μm. In yet other embodiments, the thickness of gas permeable material separating any chamber for gas flow in the microfluidic device from a chamber for fluid flow in the microfluidic device is about 10 μm to about 25 μm.

III. Chamber Features

Chamber features can be characterized according their physical dimensions, topographic features, and presence of modifications to the surface of the chamber. Various aspects of the chamber features are described below.

A. Height, Width, and Length of Chambers

Chambers can be characterized according to the height, width, and/or length of the chambers. The particular combination of height, width, and length of the chambers can impact the surface area of the chamber, flow properties of fluid or gas passing through a chamber, and pressure that may be required in order to drive fluid or gas through the chamber.

Regarding height of a chamber, in certain embodiments, any chamber for fluid flow has a height less than 600 μm, 500 μm, 400 μm, 300 μm, 200 μm, 100 μm, 75 μm, 50 μm, 25 μm, or 15 μm. In certain embodiments, any chamber for fluid flow has a height less than 25 μm. In certain embodiments, any chamber for fluid flow has a height of about 10 μm to about 15

μm. In certain embodiments, the height of any chamber for gas flow has the same height as any chamber for fluid flow in the same layer.

Regarding width of a chamber, in certain embodiments, any chamber for fluid flow has a width of less than 600 μm, 500 μm, 400 μm, 300 μm, 200 μm, 150 μm, 100 μm, or less than 50 μm. In certain embodiments, any chamber for fluid flow has a width of less than 200 μm. In certain embodiments, any chamber for fluid flow has a width of about 200 μm to about 10 μm, or about 150 μm to about 50 μm. In certain embodiments, the width of any chamber for gas flow has the same width as any chamber for fluid flow in the same layer. In certain other embodiments, any chamber for fluid flow has a width to height ratio of at least 2 to 1.

Regarding length of a chamber, in certain embodiments, any chamber for fluid flow has a length less than 2 cm, 5 cm, 7 cm, 10 cm, or 15 cm. In certain embodiments, any chamber for fluid flow has a length in a range of about 2 cm to 15 cm, or about 5 cm to about 10 cm.

The chamber(s) for fluid flow can also be characterized according to the fluid shear rate at the wall of the chamber observed as a fluid travels through the chamber(s). In certain embodiments, any chamber for fluid flow is characterized as having a fluid shear rate in the range of about $100\ s^{-1}$ to about $4000\ s^{-1}$ for blood at 37.0° C., a range of about $100\ s^{-1}$ to about $3000\ s^{-1}$ for blood at 37.0° C., a range of about $400\ s^{-1}$ to about $2200\ s^{-1}$ for blood at 37.0° C., a range of about $1000\ s^{-1}$ to about $2200\ s^{-1}$ for blood at 37.0° C., a range of about $1500\ s^{-1}$ to about $2200\ s^{-1}$ for blood at 37.0° C., or a range of about $1900\ s^{-1}$ to about $2200\ s^{-1}$ for blood at 37.0° C.

The chamber(s) for fluid flow can also be characterized according to the quantity of fluid that can be transported through a population of said channels. For example, in certain embodiments, a population of 8000 to 9000 of chambers for fluid flow can transport blood at a rate of about 1 mL/min to about 500 mL/min, about 1 mL/min to about 100 mL/min, or about 50 mL/min to about 500 mL/min. In certain other embodiments, the microfluidic device contains a plurality of chambers for fluid flow that, collectively, are configured to transport fluid in an amount of about 1 mL/min to about 500 mL/min through said plurality of chambers for fluid flow.

B. Cross-Sectional Characterization of Chambers

It is contemplated that chambers with various types of cross-sections are amenable for use in the microfluidic devices described herein. For example, in certain instances, the chambers may be rectangular, round, triangular, semi-circular, or other geometries. Chambers having a rectangular cross-sectional geometry are shown in FIG. 1B and chambers having at least one semi-circular cross-sectional geometry is shown in FIG. 1C. It is contemplated that certain cross section geometries described herein can minimize shear stress experienced by fluid, e.g., blood, traveling through fluid chamber(s) in the device. For example, it is completed that rounded or semi-circular cross sectional geometries can minimize shear stress experienced by a fluid traveling through the chamber(s) and enhance the surface-to-volume ratio of the chamber. Accordingly, in certain embodiments, any chamber for fluid flow has a cross-section that is semi-circular.

Further, the cross-section geometry of a fluid chamber can be selected in order to minimize the pressure that must be exerted on the fluid, e.g., blood, in order to force the fluid through the microfluidic device. Cross section geometries that promote fluid transfer through the chamber with minimal friction with the walls of the chamber are completed to minimize the pressure that must be exerted on the fluid in order to force the fluid through the microfluidic device. In addition, cross section geometries that promote fluid transfer by minimizing loses associated with layers of fluid moving through the chambers are completed to minimize the pressure that must be exerted on the fluid in order to force the fluid through the microfluidic device.

C. Topographic Features of Chambers

Chambers may contain three-dimensional structures to, for example, induce fluid mixing, or to achieve other particular performance properties. Structures that induce fluid mixing can include topographic features directing fluid out of line with the flow direction (such as cross-hatched patterns or ridges placed diagonal to the flow), flexible elements that deform under the flow to create temporal perturbations in the fluid, and elements that induce rotational flows within the flow stream. Accordingly, in certain embodiments, a chamber for fluid flow further comprises a mixing element to induce fluid mixing. In certain other embodiments, a chamber for fluid flow comprises one or more changes in height or width of the chamber along the longitudinal axis of the chamber.

Another feature of the chambers relates to two-dimensional structures, such as, networks of branched or bifurcated channels. The networks may feature smooth bifurcations and/or gradual changes in the cross-sectional channel dimensions, and may mimic the physiological properties of in-vivo vascular and/or micro-vascular networks. Above and below a "vascular layer" that contains the fluid-carrying channel networks, oxygen chambers may be located. Such networks with dual-sided oxygen chambers may double the transfer efficiency of oxygen (and/or other gases) into and out of the fluid-containing chambers. In some embodiments, the chambers are formed by patterns of posts, instead of branched channels, in the vascular layer (i.e., by blocks of material that connect the layers above and below the vascular layer). For example, the post may be arranged at the vertices of a square lattice, leaving a latticework of channels in between. In certain embodiments, the posts are hollowed out and carry oxygen as an additional source through the vascular layers. For example, the hollowed out posts may be fluidically connected to oxygen chambers above and below the vascular layer that the posts reside in, such that oxygen enters the vascular layer both from the upper and lower oxygen chambers and also through the walls of the posts.

D. Modifications to the Surface of Chambers

The inner surface of chambers can be modified to achieve certain performance properties, such as improved resistance to degradation caused by a particular substance that may be present in the fluid or gas, or reduce the risk that the chamber may cause a transformation (e.g., inducement of blood clotting) of certain components in the fluid or gas. The surface modification may be a partial coating of the inner wall of the chamber with a particular substance or a complete coating of the inner wall of the chamber with a particular substance. Surface modifications that alter blood-material interactions can include surface-tethered compounds that reduce clotting (such as heparin), hydrophobic/hydrophilic monolayers that control protein adsorption to the device, degradable coatings that reduce build-up of adsorbed species in the device, and energetic treatments (such as energetic oxygen plasma) that alter surface chemistry and subsequent hydrophobicity/hydrophilicity. In certain embodiments, any chamber for fluid flow is coated with a biological molecule, such as serum albumin or a surface protein that can be found in vasculature. In certain embodiments, any chamber for fluid flow is coated with an anti-coagulant (such as heparin), which is contemplated to reduce blood clotting in fluid chambers for blood flow.

IV. Distribution System for Delivering Fluid and Gas to the Microfluidic Device The microfluidic device may comprise a distribution system for delivering gas to any gas chamber in the device, and delivering fluid to any fluid chamber in the device. The distribution system may comprise branching or bifurcating microchannels, biomimetic vascular-like channels, or a manifold structure. Controllable access to the chambers may be provided by vascular-like channel structures, structures that provide a smooth path for fluid flow, or other configurations.

Accordingly, in certain embodiments, the microfluidic device further comprises means for delivering gas to the chamber for fluid flow and fluid to the chamber for fluid flow. In certain embodiments, the delivery means bridge large to small conduits.

V. Fluid Conduits and Pumps

The microfluidic devices described herein may optionally contain one or more of: (i) a first access conduit affording fluid communication with an input end of one or more chambers for fluid flow; (ii) a first return conduit affording fluid communication with an output end of one or more chambers for fluid flow; (iii) a first pump for ensuring that a fluid entering the first access conduit flows through one or more chambers for fluid flow and out the first return conduit, (iv) a first access conduit affording fluid communication with an input end of one or more chambers for gas flow; and (vi) a second pump for ensuring that a gas entering the first access conduit flows through one or more chambers for gas flow.

Access and return conduits can convey fluid, such as patient blood, to and from the chamber(s) for fluid flow. Access may be through an IV needle, cannulae, fistula, catheter, or an implanted access device. The access points may be existing points for previous treatments (e.g., hemodialysis) and may be arterio-venous or veno-venous in nature. The conduits can be standard medical tube materials including polymers such as silicone rubber, polyurethane, polyethylene, polyvinyl chloride, and latex rubber. An approximate size range of the inner diameter of the access conduits can be 300 µm-1 cm. The access conduits can be integrated into the microfluidic device, or can instead be separate and have attachment points to connect to the microfluidic device.

A pump may regulate blood flow rate into the device, e.g., if arterial blood pressure is not high enough for the particular application or if a venous-venous access is deemed more desirable. In some cases, a physiological blood pressure of 120 mmHg may be sufficient to drive blood flow from an arterial access through the microfluidic device and back to the patient. In other cases, particularly where veno-venous access is used, a pump is used to drive blood through the microfluidic device. Although optimal pump pressure depends on the desired blood flow, pump pressures ranging from 0-300 mmHg are representative.

VI. Reservoir for Gas Storage

The microfluidic device may optionally comprise a reservoir for gas storage. In certain embodiments, the reservoir is an extension of at least one chamber for gas flow. In certain embodiments, the reservoir contains oxygen.

VII. Gas Permeable Materials for Microfluidic Devices

Various gas permeable polymeric materials are known in the art for use in microfluidic devices and are contemplated to be amenable for use in the microfluidic devices described herein. For example, in certain embodiments, the gas permeable material is an organosilicone polymer (e.g., polysiloxane, PDMS variants such as MDX-4, and modified PDMS compositions that enhance gas (e.g., oxygen and carbon dioxide) permeability), polyethylene, or polyurethane. In certain particular embodiments, the gas permeable material is polydimethylsiloxane.

VIII. Gases and Fluids for Use with the Microfluidic Devices

The microfluidic devices described herein are contemplated to be amenable for use with a wide variety of fluids and gases. For example, in certain embodiments, the gas is oxygen, carbon dioxide, air, nitrogen, or an inert gas. In certain embodiments, the fluid is an aqueous solution, blood, an organic solvent, or the like. In certain embodiments, the chamber for fluid flow comprises blood, and the chamber for gas flow comprises oxygen. In certain other embodiments, the chamber for gas flow comprises at least one of oxygen, carbon dioxide, air, nitrogen, an inert gas, or a partial vacuum. In certain embodiments, cellular components are temporarily removed from the blood before the blood is passed through the microfluidic device, then the cellular components are reintroduced to the blood that has passed through the microfluidic device—this is contemplated to reduce the potential for blood coagulation within the microfluidic device.

IX. Preparation of Microfluidic Devices

Microfluidic devices containing one or more layers may be prepared using microfabrication methods where a gas permeable polymer is molded to a microfabricated mold. For example, polydimethylsiloxane (PDMS) may spin-coated onto the mold, as shown in FIG. 3. However, other gas permeable polymers may be employed as well, including, but not limited to, other organosilicone materials (e.g., polysiloxane, PDMS variants such as MDX-4, and modified PDMS compositions that enhance gas (e.g., oxygen and carbon dioxide) permeability), polyethylene, and polyurethane-like materials.

The mold used above may be created through microfabrication, typically photopatterned photoresist; however, etched silicon, cured epoxy, and/or electroformed metal can also be used. Prepolymer is then poured into the mold, and the mold is spun at a specific speed to create a thin layer of the prepolymer. The prepolymer is then cured, and the device released from the mold after curing.

An alternative method to create the chamber layers is to apply pressure to the prepolymer in the mold from above using a second microfabricated mold. This replaces the spin coating step, and the device is cured and then released from the molds.

Polymer layers containing flow chambers prepared using the above procedures are then aligned using techniques that include visual alignment and/or alignment via mechanical locating devices. Visual alignment may be achieved by using alignment marks or fiducials integrated into the layers that serve to guide layer alignment for assembly. The alignment may involve magnifying the view of the device layers and any alignment marks, a mechanism to move the layers relative to each other very precisely, and a means of bonding the layers together either permanently or temporarily. In one embodiment, the alignment process is similar to the alignment of a mask to a patterned silicon wafer as used in typical microfabrication processes, yet permits the alignment and bonding of polymer layers. Alignment via mechanical locating devices may be achieved by using specific locking elements integrated into the layers, such that the locating devices on the top of a first layer align and lock with the locating devices on the bottom of a second layer directly above the first layer. In one embodiment, the mechanical locating devices require very little active alignment, as they provide specific and precise location of one layer with respect to another layer.

Once the polymer layers are aligned, they may then be bonded together using bonding methods that include plasma activation bonding, adhesive bonding, and/or mechanical clamping. FIG. 4 depicts cross-sectional views of an exemplary two layer device that has been fabricated using these techniques.

Various embodiments of the device described herein may include a single layer possessing multiple chambers, multiple stacked layers with multiple chambers in each layer, a single layer rolled into a tubular shape, or other configurations. Each layer may feature various channel cross sections and flow path geometries. A variety of methods may be employed to connect either gas or fluid flow to the chambers. In one embodiment, the gas and fluid flow chambers are arrayed in an alternating or complex fashion, and the gas or fluid is precisely delivered from a main access conduit of large cross sectional area to the individual chambers having very low cross sectional area. The precise delivery can take the form of branching or bifurcating microchannels, biomimetic vascular-like channels, and/or a manifold structure. The connectivity bridges large to small conduits, and may reduce harmful blood-material or blood-flow induced shear stress interactions by precisely varying flow conditions through flow channel geometry.

Accordingly, one aspect of the invention provides a method of manufacturing a microfluidic device, comprising forming a first layer of a single type of gas permeable material that defines therein at least one chamber for gas flow and at least one chamber for fluid flow, wherein the thickness of gas permeable material separating any chamber for gas flow from an adjacent chamber for fluid flow is about 10 µm to about 100 µm.

In certain embodiments, the method further comprises forming at least one chamber for gas flow and at least one chamber for fluid flow in at least one additional layer of a single type of gas permeable material. In certain embodiments, the method further comprises coupling additional layers of the single type of gas permeable material to the first layer. In certain embodiments, the layers of gas permeable material are stacked.

X. Medical and Other Applications For Microfluidic Devices

Various embodiments of the invention are contemplated to reduce side effects while improving gas transfer efficiency, thereby allowing expansion into markets where long-term use is required for a high capacity lung assist device. Commercial applications for embodiments of the invention include extracorporeal membrane oxygenation (ECMO), cardiopulmonary bypass (CPB), lung assist for patients with lung damage or adult respiratory distress syndrome (ARDS), bridging patients from injury to lung transplant, treatment of chronic obstructive pulmonary disease, enhanced oxygenation or carbon dioxide removal for fire/blast victims, and eventual long-term partial or complete lung replacement, among others.

Accordingly, one aspect of the invention provides a method for transferring a gas to a fluid. The methods comprises passing a fluid through a microfluidic device described herein, such as any of the microfluidic devices described in Sections I-IX, having a gas in at least one chamber for gas flow, to thereby transfer said gas to said fluid. In certain embodiments, said fluid is blood, and said gas comprises oxygen. In certain embodiments, the microfluidic device is fluidly connected to the blood vasculature of a patient. In certain embodiments, the method further comprises transferring a gas dissolved in said fluid to a chamber for gas flow in the microfluidic device.

XI. Definitions

To facilitate an understanding of the present invention, a number of terms and phrases are defined below.

The terms "a," "an" and "the" as used herein mean "one or more" and include the plural unless the context is inappropriate.

The term "plurality" refers to at least four. For example, a layer containing a plurality of chambers refers to layer containing at least four chambers.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A microfluidic device, comprising:
a first layer of a single type of gas permeable material that defines therein at least two chambers configured for gas flow and at least two chambers configured for liquid flow, wherein the at least two chambers configured for liquid flow are configured differently than the at least two chambers configured for gas flow and the thickness of the gas permeable material separating a chamber configured for gas flow from an adjacent chamber configured for liquid flow is about 1 µm to about 100 µm; and
a second layer of the gas permeable material, stacked upon the first layer, defining therein at least two chambers for gas flow and at least two chambers for liquid flow, wherein at least one chamber configured for liquid flow in the first layer is (i) adjacent to and in-plane with at least one chamber configured for gas flow in the first layer and (ii) aligned, in a plane perpendicular to the first layer, with a chamber configured for gas flow in the second layer.

2. The microfluidic device of claim 1, wherein the first layer defines therein a plurality of chambers for gas flow and a plurality of chambers for liquid flow.

3. The microfluidic device of claim 1, wherein any chamber for gas flow and at least one chamber for liquid flow are arranged such that flow directions for the gas and the liquid are parallel or antiparallel to one another.

4. The microfluidic device of claim 1, wherein at least one chamber configured for gas flow is arranged such that the flow direction of gas is transverse to the direction of liquid flow in the chamber configured for liquid flow.

5. The microfluidic device of claim 1, further comprising a third layer of a single type of gas permeable material stacked upon the second layer, where the third layer defines therein at least one chamber configured for gas flow and at least one chamber configured for liquid flow.

6. The microfluidic device of claim 1, wherein the thickness of the gas permeable material separating a chamber configured for gas flow in the second layer from a chamber configured for liquid flow in the second layer is about 1 µm to about 100 µm.

7. The microfluidic device of claim 1, wherein the thickness of gas permeable material separating at least one chamber configured for gas flow in the microfluidic device from a chamber configured for liquid flow in the microfluidic device is about 10 µm to about 100 µm.

8. The microfluidic device of claim 1, wherein the thickness of gas permeable material separating at least one chamber configured for gas flow in a layer from a chamber configured for liquid flow in the same layer is about 50 µm to about 100 µm.

9. The microfluidic device of claim 1, wherein the thickness of gas permeable material separating at least one chamber configured for gas flow in the microfluidic device from a chamber configured for liquid flow in the microfluidic device is about 10 µm to about 25 µm.

10. The microfluidic device of claim 1, wherein at least one liquid chamber has a height less than 25 µm.

11. The microfluidic device of claim 1, wherein at least one liquid chamber has a height of about 10 µm to about 15 µm.

12. The microfluidic device of claim 1, wherein at least one liquid chamber has a width of less than 200 µm.

13. The microfluidic device of claim 1, wherein the liquid chamber has a width to height ratio of at least 2 to 1.

14. The microfluidic device of claim 1, wherein the gas permeable material is an organosilicone polymer, polyethylene, or polyurethane.

15. The microfluidic device of claim 1, wherein the gas permeable material is polydimethylsiloxane.

16. The microfluidic device of claim 1, wherein the chamber configured for liquid flow comprises blood, and the chamber configured for gas flow comprises oxygen.

17. A microfluidic device, comprising:
a first layer of a single type of gas permeable material that defines therein at least two chambers configured for gas flow and at least two chambers configured for liquid flow, wherein the at least two chambers configured for liquid flow are configured differently than the at the at least two chambers configured for gas and the thickness of the gas permeable material separating a chamber configured for gas flow from an adjacent chamber configured for liquid flow is no greater than that which has an oxygen gas permeance of at least $1\times10^{-6}$ mL/s/cm$^2$/cm Hg; and
a second layer of the gas permeable material, stacked upon the first layer, defining therein at least two chambers for gas flow and at least two chambers for liquid flow, wherein at least one chamber configured for liquid flow in the first layer is (i) adjacent to and in-plane with at least one chamber configured for gas flow in the first layer and (ii) aligned, in a plane perpendicular to the first layer, with a chamber configured for gas flow in the second layer.

18. A method for transferring a gas to a liquid, comprising:

passing a liquid through at least two chambers configured for liquid flow located in a microfluidic device; and flowing a gas through at least two chambers configured for gas flow located in the microfluidic device, wherein the microfluidic device comprises:

a first layer of a single type of gas permeable material that defines therein a plurality of chambers configured for gas flow and a plurality of chambers configured for liquid flow, wherein the plurality of chambers configured for liquid flow are configured differently than the plurality of chambers configured for gas flow, and the thickness of the gas permeable material separating a chamber configured for gas flow from an adjacent chamber configured for liquid flow is about 1 µm to about 100 µm; and a second layer of the gas permeable material, stacked upon the first layer, defining therein a plurality of chambers for gas flow and a plurality of chambers for liquid flow, wherein at least one chamber configured for liquid flow in the first layer is (i) adjacent to and in-plane with at least one chamber configured for gas flow in the first layer and (ii) aligned, in a plane perpendicular to the first layer, with a chamber configured for gas flow in the second layer.

19. The method of claim 18, wherein said chamber configured for liquid is configured for carrying blood, and said gas comprises oxygen.

20. The method of claim 19, wherein the microfluidic device is fluidly connected to the blood vasculature of a patient.

21. The method of claim 18, further comprising transferring a gas dissolved in said liquid to a chamber configured for gas flow in the microfluidic device.

* * * * *